United States Patent [19]

Davidson

[11] Patent Number: 4,476,059

[45] Date of Patent: Oct. 9, 1984

[54] CHLOROACETONITRILE SYNTHESIS

[75] Inventor: Robert I. Davidson, Baton Rouge, La.

[73] Assignee: Ethyl Corporation, Richmond, Va.

[21] Appl. No.: 509,249

[22] Filed: Jun. 30, 1983

[51] Int. Cl.$^3$ .................. C07C 120/00; C07C 121/16
[52] U.S. Cl. ............................ 260/465.7; 260/465 G
[58] Field of Search ...................................... 260/465.7

[56] References Cited

U.S. PATENT DOCUMENTS 2,331,681 10/1943 Hechenbleikner ............... 260/465.7
3,118,926 1/1964 Horrom ............................ 260/465.2
4,371,705 2/1983 Davis, Jr. ......................... 260/465.7

OTHER PUBLICATIONS

Davies, et al., Journal of the Chemical Society, (1951), pp. 2595–2597.
Weygand/Hilgetag, "Preparative Organic Chemistry", (1972), pp. 222–223, John Wiley and Sons, N.Y.

*Primary Examiner*—Joseph Paul Brust
*Attorney, Agent, or Firm*—Donald L. Johnston; John F. Sieberth; Patricia J. Hogan

[57] ABSTRACT

A 2-hydroxyacetonitrile is reacted with thionyl chloride in the presence of a trialkylamine and a suitable solvent to form a 2-chloroacetonitrile. In a preferred embodiment of the invention, 2-chloropropionitrile is prepared by reacting lactonitrile with an excess of thionyl chloride in the presence of triethylamine and dichloromethane.

4 Claims, No Drawings

CHLOROACETONITRILE SYNTHESIS

FIELD OF THE INVENTION

This invention relates to 2-chloroacetonitriles and a process for preparing them.

BACKGROUND

As disclosed in W. Davies et al., *Journal of the Chemical Society*, 1951, pp. 2595-2598, it is known that 2-chloropropionitrile can be prepared by adding thionyl chloride to a mixture of lactonitrile and pyridine. To date, this has been the best method of producing 2-chloroacetonitriles on a large scale, even though it has led to the formation of a very thick slurry and has produced an isolated yield of only 50% after two distillations. It would obviously be desirable to find a way of improving this technique so as to improve processing and provide higher yields of 2-chloroacetonitriles.

SUMMARY OF THE INVENTION

An object of this invention is to provide a novel process for preparing 2-chloroacetonitriles.

Another object is to provide such a process which permits the preparation of 2-chloroacetonitriles in high yields.

A further object is to provide such a process particularly useful for the preparation of 2-chloropropionitrile.

These and other objects are attained by reacting a 2-hydroxyacetonitrile with thionyl chloride in the presence of a trialkylamine and a solvent to form a 2-chloroacetonitrile.

DETAILED DESCRIPTION

2-Hydroxyacetonitriles useful in the practice of the invention are compounds corresponding to the formula:

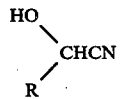

wherein R is an innocuous alkyl or aryl (e.g., phenyl, naphthyl, etc.) group, i.e., a substituted or unsubstituted alkyl or aryl group containing no substituents which would interfere with the reaction. Generally R is an alkyl group containing about 1-10 carbons. The preferred 2-hydroxyacetonitrile is lactonitrile, i.e., a compound corresponding to the above formula in which R is methyl.

The thionyl chloride is ordinarily used in excess of the molar equivalent amount required to react with the 2-hydroxyacetonitrile—at least about 1.2 molar proportions of thionyl chloride per molar proportion of 2-hydroxyacetonitrile generally being most desirable.

The trialkylamine employed in the practice of the invention instead of the pyridine of the prior art may be any trialkylamine in which the alkyl groups contain about 1-6 carbons, but it is preferably triethylamine. Although larger amounts may be employed when desired, this component is ordinarily used in an amount such as to provide about one molar proportion of trialkylamine per molar proportion of 2-hydroxyacetonitrile.

In the process of the invention, the reactants are combined in the presence of a suitable diluent, such as dichloromethane, and are reacted for a suitable time, e.g., about one hour, generally at reflux temperatures. The reaction product is then worked up to isolate the desired product, which may be recovered by distillation. To obtain optimum yields it is preferred to neutralize the reaction mixture prior to workup.

The invention is advantageous in that it leads to the production of 2-chloroacetonitriles in high yields without the undue slurry build-up and resultant processing difficulties that were encountered in the process of Davies et al.

The following example is given to illustrate the invention and is not intended as a limitation thereof.

EXAMPLE

A suitable reaction vessel was charged with one molar proportion of distilled lactonitrile and about four molar proportions of dichloromethane, to which one molar proportion of triethylamine was added with ice bath cooling. The reaction mixture was cooled to 5° C. under nitrogen, and 1.2 molar proportions of thionyl chloride were added over a period of two hours while keeping the pot temperature below 25° C. When the addition was complete, the resulting light brown slurry was heated to reflux for one hour, and the dark brown solution thus produced was cooled and neutralized to a pH of 7 with 10% sodium hydroxide.

The organic phase was separated and extracted with saturated sodium chloride solution, dried over anhydrous sodium sulfate, filtered, and concentrated by distillation through a four-inch Vigreaux column. The crude product was then purified by distillation through an Oldershaw column to afford a 90% yield of 2-chloropropionitrile, a colorless liquid distilling at 120°-125° C. The analytical yield was close to quantitative.

It is obvious that many variations can be made in the products and processes set forth above without departing from the spirit and scope of this invention.

I claim:

1. A process which comprises reacting one molar proportion of lactonitrile with at least about 1.2 molar proportions of thionyl chloride in the presence of dichloromethane and at least one molar proportion of a trialkylamine to form 2-chloropropionitrile and then neutralizing the product.

2. The process of claim 1 wherein the trialkylamine is triethylamine.

3. The process of claim 1 wherein the reaction is conducted at reflux temperatures.

4. The process of claim 1 wherein one molar proportion of lactonitrile is reacted with at least about 1.2 molar proportion of thionyl chloride at reflux temperatures in the presence of dichloromethane and about one molar proportion of triethylamine.

* * * * *